United States Patent
Kohout

(10) Patent No.: US 6,432,125 B2
(45) Date of Patent: Aug. 13, 2002

(54) ABSORBENT THERMAL BAG

(75) Inventor: Daniel Kohout, Franklin, KY (US)

(73) Assignee: Allegiance Corporation, McGaw Park, IL (US)

( * ) Notice: Subject to any disclaimer, the term of this patent is extended or adjusted under 35 U.S.C. 154(b) by 40 days.

(21) Appl. No.: 09/793,069

(22) Filed: Feb. 26, 2001

Related U.S. Application Data

(63) Continuation-in-part of application No. 09/302,730, filed on Apr. 30, 1999.

(51) Int. Cl.$^7$ ................................................. A61F 7/00
(52) U.S. Cl. ......................................... 607/114; 607/96
(58) Field of Search ............................ 607/96, 108–114

(56) References Cited

U.S. PATENT DOCUMENTS

| | | |
|---|---|---|
| 3,643,665 A | 2/1972 | Caillouette |
| 3,867,939 A | 2/1975 | Moore et al. |
| 3,871,376 A | 3/1975 | Kozak |
| 3,889,684 A | 6/1975 | Lebold |
| 3,913,559 A * | 10/1975 | Dandliker .............. 126/263.07 |
| 4,106,477 A * | 8/1978 | Feld .............. 126/204 |
| 4,240,436 A | 12/1980 | Singleton |
| 4,381,025 A | 4/1983 | Schooley |
| 4,385,950 A | 5/1983 | Hubbard et al. |
| 4,397,315 A | 8/1983 | Patel |
| 4,404,820 A | 9/1983 | Romaine |
| 4,596,250 A * | 6/1986 | Beisang et al. ............. 607/114 |
| 4,605,006 A | 8/1986 | Jacques |
| 4,607,624 A | 8/1986 | Jefferson |
| 4,776,042 A | 10/1988 | Hanson et al. |
| 4,953,550 A | 9/1990 | Dunshee |
| 5,062,425 A | 11/1991 | Tucker |
| 5,123,411 A | 6/1992 | Noziri |
| 5,133,348 A | 7/1992 | Mayn |
| 5,165,402 A | 11/1992 | McCoy |
| 5,167,655 A | 12/1992 | McCoy |
| 5,178,139 A | 1/1993 | Angelillo et al. |
| 5,245,938 A | 9/1993 | Frye |
| 5,277,180 A | 1/1994 | Angelillo et al. |
| 5,300,103 A | 4/1994 | Stempei et al. |
| 5,356,426 A | 10/1994 | Delk et al. |
| 5,447,531 A | 9/1995 | Wood |
| 5,447,532 A | 9/1995 | Furuya |
| 5,456,704 A | 10/1995 | Kilcullen |
| 5,478,988 A | 12/1995 | Hughes et al. |
| 5,486,206 A | 1/1996 | Avery |
| 5,641,325 A | 6/1997 | Delk et al. |
| 5,702,375 A | 12/1997 | Angelillo et al. |
| 5,707,645 A | 1/1998 | Wierson |
| 5,723,002 A | 3/1998 | Delk et al. |
| 5,817,150 A | 10/1998 | Owens |
| 5,984,953 A | 11/1999 | Sabin et al. |

* cited by examiner

Primary Examiner—Roy D. Gibson
(74) Attorney, Agent, or Firm—Andrew G. Rozycki

(57) ABSTRACT

An absorbent thermal bag made in accordance with the principles of the present invention includes an absorbent pad operatively associated with a thermal bag which can be regenerated in situ. The junction of the absorbent pad and the thermal bag defines an unobstructed perimeter area that is an area of the absorbent pad that extends beyond the thermal bag. The unobstructed perimeter area provides an area of improved absorption and allows the side-by-side simultaneous placement of the thermal bag and the absorbent pad on a wound site. The thermal bag can contain endothermic materials such as ice for cold therapy or, alternatively, exothermic materials for heat therapy.

53 Claims, 6 Drawing Sheets

ABSORBENT THERMAL BAG

RELATED APPLICATION DATA

This application is a continuation-in-part of U.S. patent application Ser. No. 09/302,730 filed Apr. 30, 1999, now awaiting issuance.

FIELD OF THE INVENTION

This invention relates to a low cost thermal bag that provides improved absorption of body fluids. This invention further relates to an absorbent thermal bag product that is refillable and may be regenerated in situ.

BACKGROUND OF THE INVENTION

The use of cold packs and hot packs for thermal therapy is known. Cold and hot packs may be of several general types. One type of cold pack contains an insulating material which, upon cooling in a refrigerator or freezer, gradually warm back to ambient temperature. Similarly, one type of hot pack contains an insulating material and can be warmed. Another type of thermal pack operates via a change of phase of the components of the pack. Still another type of thermal pack employs chemical components that are endotherm-producing in the case of cold packs, or exotherm-producing in the case of hot packs, on dissolution in a solvent.

Phase change materials may be converted between solid and liquid phase and utilize a latent heat of fusion to absorb, store and release heat, or cool, during such phase conversion. Ice/water is one example of phase change material.

Certain chemical compounds, once dissolved into a solution, result in either a lowering of the temperature of the solution below or above ambient temperature. On dissolution, these compounds absorb heat from, or expend heat to, the surrounding environment. For example, inorganic salts or soluble organic compounds known to have positive enthalpy of aqueous solution are used to make the reduced temperature solutions useful in cold packs. In the case of hot packs, compositions having negative enthalpy of aqueous solution are used to produce increased temperature solutions useful for hot packs.

Examples of cold packs that employ an insulating material are cold packs that contain a gel. Typically, these cold packs are cooled in a refrigerator or freezer. For cold therapy, once cooled, the cold pack is placed on the injured or sore area and thus provides the cold therapy.

Chemical cold packs that provide an insulating layer between the cold pack and the skin are also known. One such cold pack uses an outer pouch containing capillaries to allow drainage of the pack and to provide a temperature moderating effect. Another chemical cold pack uses a wetting member in contact with the chemical cold pack, thereby providing moist cold to an injury. Yet another chemical cold pack positions an absorbent/insulating layer between the chemical cold and the ambient air with the chemical cold pack placed up against the patient's skin. In this device, the surface area of the absorbent/insulating layer is smaller than the surface area of the cold pack. One prior art chemical cold pack cover provides means to attach the cold pack to a patient and to provide a water-resistant material in contact with the skin.

One disadvantage of the prior art devices is that the thermal packs may not easily be regenerated in situ. Additionally, the prior art devices are not readily reusable for a single application. Another disadvantage of the prior art devices is that the insulating materials, while possessing at least some absorbency, are positioned away from the injury. A further disadvantage of the prior art devices is that the absorbency of the absorbent/insulating layer is obstructed by the larger thermal pack surface area. Yet another disadvantage of the prior art devices is that they are costly to manufacture.

It would therefore be an advantage to have a cold or hot pack that can be easily regenerated in situ. It would be a further advantage to have a cold or hot pack that would allow the simultaneous placement of the thermal pack and absorbent pad on the injury site. It would be yet a further advantage to provide a low cost thermal pack that can be regenerated in situ and allows the simultaneous placement of the pack and the absorbent pad on the injury site.

SUMMARY OF THE INVENTION

The present invention provides a thermal pack, i.e., a cold or hot pack, that can be regenerated in situ. The present invention provides a thermal pack that allows the simultaneous placement of the pack and an absorbent pad on the injury site. The present invention further provides a low cost thermal pack that can be regenerated in situ and allows the simultaneous placement of the thermal pack and the absorbent pad on the injury site.

The present invention provides an absorbent thermal bag that includes a thermal bag and an absorbent pad attached to the thermal bag. One side of the thermal bag defines a single-side surface area, while one side of the absorbent pad defines a pad area. The thermal bag has a resealable opening. The pad area is larger than the single side surface area, and the difference in the areas provides an unobstructed perimeter. Phase change material or other temperature modifying materials can be added to the thermal bag through the resealable opening and the unobstructed perimeter area provides an unobstructed area for absorbing a bodily fluid on the absorbent pad.

In one embodiment of the invention, the absorbent thermal bag comprises a thermal bag which is an ice bag adapted to receive an endothermic material, such as a phase change material. In an alternative embodiment, the absorbent thermal bag comprises a thermal bag adapted to receive an exothermic material, such as an exotherm producing composition or warm water.

DETAILED DESCRIPTION OF THE INVENTION

The term "thermal" when used in the context of the invention is meant to refer to the capability of temperature modifications, both in terms of increases or decreases in temperature. The term when used in reference to the "thermal bag" for purposes of the invention indicates that the bag component of the absorbent thermal bag of the invention accommodates either endothermic or exothermic materials to render the deliver the desired cold or heat therapy, respectively. Several of the figures depict the thermal bag as an ice bag containing ice and water, which is intended for illustrative purposes only.

Figure 1:
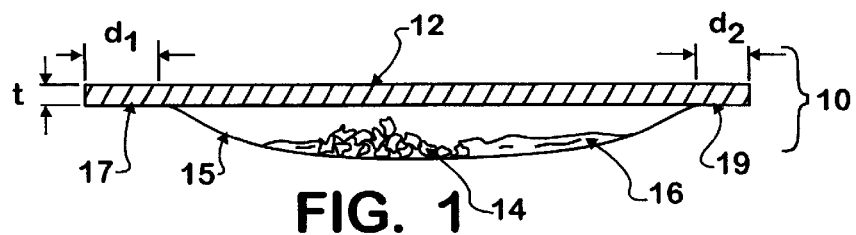
FIG. 1 is a cross-sectional schematic of an absorbent thermal bag made in accordance with the principles of the present invention.

Referring to FIG. 1, an absorbent thermal bag made in accordance with the principles of the present invention is designated by 10. In this embodiment depicted, the absorbent thermal bag 10 includes an absorbent pad 12 operatively associated with an ice bag 15. The ice bag 15 defines a single-side surface area that is the surface area of one side of the ice bag 15. The absorbent pad 12 defines a pad area that is the surface area of one side of the absorbent pad 12. The junction of the absorbent pad 12 and the ice bag 15 defines attachment sections 17, 19. The absorbent pad 12 extends beyond the ice bag 15 a perimeter distance $d_1$, at attachment section 17 and a perimeter distance $d_2$ at attachment section 19. The perimeter distances di and $d_2$ will be more fully described below. The absorbent pad 12 defines a thickness t. The thickness t may range from about 0.0625 inches to about 1 inch (about 0.3175 cm to about 2.5400 cm), and more, and preferably from about 0.250 inches to about 0.750 inches (about (0.6350 cm to about 1.9050 cm).

The ice bag 15 may contain ice 14, other suitable phase change materials, or materials which absorb heat. The ice bag 15 may also contain water 16, or other liquid that results from melting of the phase change material. In the case of a thermal bag for heat therapy or storage, the bag contains an exothermic material instead of an "ice bag." The thermal bag, therefore, can contain exothermic (heat releasing) materials or compositions.

Suitable exothermic materials which can be used in conjunction with the invention include exothermic phase change materials, exothermic dissolving solute in solvent compositions, and latent heat storage materials. Examples of exothermic phase change materials include, but are not limited to, sodium thiosulfate pentahydrate and sodium acetate trihydrate. Examples of exothermic dissolving solutes in solvents which can be used include, but are not limited to, calcium chloride and water, ammonium sulfate and water, and magnesium sulfate and water. Examples of latent heat storage materials include, but are not limited to, pre-warmed water and pre-warmed oil.

Figure 2:
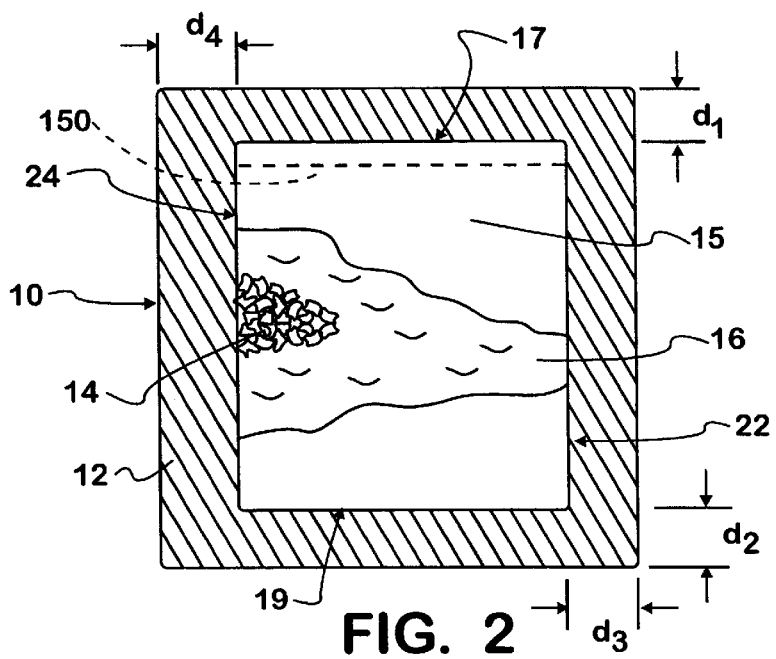
FIG. 2 is a plan view of the absorbent thermal bag of FIG. 1.

Referring now to FIG. 2, the absorbent thermal bag 10 of FIG. 1 is depicted in plan view. As illustrated, the junction of the absorbent pad 12 and the ice bag 15 also defines attachment sections 22, 24. As shown, the absorbent pad 12 extends beyond the ice bag 15 thus defining an unobstructed perimeter area. The unobstructed perimeter area is the are difference between the single-side surface area and the pad area. The unobstructed perimeter area further defines a perimeter distance $d_1$ at attachment section 17, a perimeter distance $d_2$ at attachment section 19, perimeter distance $d_3$ at attachment section 22, and a perimeter distance $d_4$ at attachment section 24. The unobstructed perimeter area provides an area of the absorbent pad 12 that is unobstructed by the ice bag 15. Unlike the prior art devices, such an unobstructed area allows for simultaneous, side-by-side placement of then ice bag 15 and the absorbent pad 12 on a wound site. Perimeter distances $d_1$, $d_2$, $d_3$ and $d_4$ may range from about 0.125 inches to about 5 inches (about 0.3175 cm to about 12.7000 cm), or more. The magnitude of the perimeter distances $d_1$, $d_2$, $d_3$ and $d_4$ may be different for different applications.

By providing an unobstructed perimeter area for absorption, the absorbent pad 12 may achieve a maximum absorbing efficiency in the unobstructed area This is contrasted with the prior art devices where an absorbent material is about the same size as an associated thermal pack, or even smaller than the associated pack, and where such an absorbent material may be even further physically constrained by a semi-permeable plastic cover. Such obstructions and constraints physically limit the extent of absorption the absorbent material undergoes and thus the absorption efficiency is reduced.

The thermal bag can be attached to the absorbent pad 12 by various means. The thermal bag may be attached to the absorbent pad using an adhesive. Alternatively, the thermal bag may be sewn to the absorbent pad, thus attaching the bag to the absorbent pad 12. In another embodiment, the perimeter portion or edges of the thermal bag can be partially or completely "tucked" under an overlapping portion of the absorbent pad.

Figure 3:
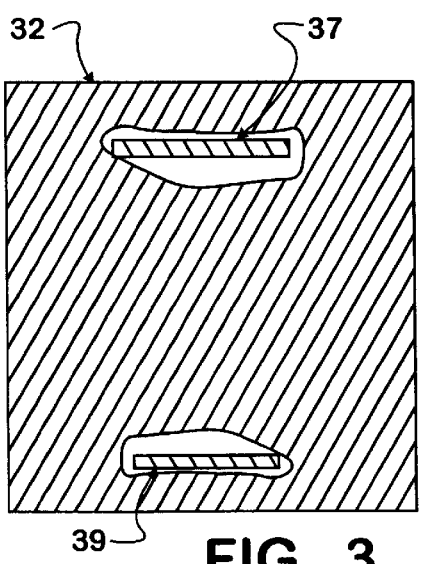
FIG. 3 is a plan view of a component of an alternative embodiment of an absorbent thermal bag of the present invention.
Figure 4:
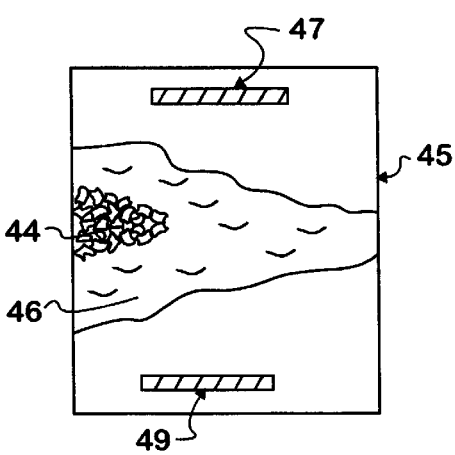
FIG. 4 is a plan view of a component of an alternative embodiment of an absorbent thermal bag of the present invention.

In one embodiment, the thermal bag is releasably attached to the absorbent pad using releasable fasteners. A preferred means for such a releasable attachment is illustrated in FIGS. 3 and 4. FIG. 3 illustrates an absorbent pad 32 that further defines hook and loop fasteners 37, 39. FIG. 4 illustrates an ice bag 45 that further defines hook and loop fasteners 47, 49. In the case of a absorbent thermal bag for cold therapy, the ice bag 45 may contain ice 44, or other suitable phase change material, and may also contain water 46, or other liquid that results from melting of the phase change material. Hook and loop fastener 37 may be operatively associated with hook and loop fastener 47 and hook and loop fastener 39 may be operatively associated with hook and loop fastener 49, so that the absorbent pad 32 is attached to the ice bag 45.

The thermal bag can be made from any waterproof material. Waterproof materials may include, for example, extruded, cast, or blown films of polyethylene, polyester, polypropylene, cellulose esters, cellulose ethers, nylon, polyvinyl alcohol acetals, polyvinyl chloride, polyvinyl chloride acetate, polystyral, methyl methacrylate, polyvinylidene chloride, and ethylene octene copolymers, and copolymers of these materials, and laminates of any of these materials. The films may be metallized. The waterproof materials may also include woven or non-woven fabrics that are made from hydrophobic materials such as nylon, polyethylene and polypropylene, and combinations of these polymers. The thermal bag 15 may also be made from a multiple ply material. One example of a multiple ply materials is a two-ply material that includes a waterproof layer and a liquid repellant layer. The waterproof layer would form the interior of the thermal bag 15 and contain the temperature modifying material. The liquid repellant layer would form the exterior of the thermal bag. The liquid repellant material may include woven or non-woven fabrics that are made from hydrophobic material such as nylon, polyethylene, polypropylene or polyvinylidene chloride, and combinations of these materials. The thermal bag 15 is resealable and, thus, has a resealable opening 150.

In the case of an absorbent ice bag, a resealable ice bag 15 allows for filling and refilling the ice bag 15 with an appropriate phase change material such as ice 14. In the case of heat therapy, a resealable thermal bag allows for filling and refilling the bag with an exothermic material, such as warm water. Thus the present invention provides an absorbent thermal bag that may be regenerated in situ. Additionally, the present invention provides an absorbent thermal bag that may be reused for a given application. For example, a phase change material or other temperature modifying material can be added to the thermal bag while the thermal bag is on a wound site.

Also, for those uses where it is not practical to add temperature modifying materials to the thermal bag in situ, the absorbent thermal bag can be removed from the wound site, refilled with a temperature modifying material, and replaced on the wound site. Any of a variety of resealable closure devices may be included with the absorbent thermal bag to provide a resealable feature to the thermal bag. The resealable closure devices may include mechanical clips, jack-knife-type safety clips, clamps, tie strings, tie straps, zippers, adhesive seals, ZIPPLOC (a registered trademark of Dow Chemical Company, Midland, Mich.), and VON-LOC (a registered trademark of Vonco Products, Inc., Lake Villa, Ill.).

In one embodiment, the thermal bag is releasably attached to the absorbent pad and the thermal bag is resealable, both configurations having been described above. This embodiment provides an absorbent thermal bag that may be practically refilled away from a wound site while the absorbent pad remains in contact with the wound site. This embodiment also provides an absorbent thermal bag that allows for easy replacement of the absorbent pad.

The absorbent pad 12 may be made from conventional cellulosic materials, such as cellulose or cellulose derivatives. Optionally, the absorbent pad 12 may be made from a combination of cellulosic material and a super absorbent polymer. Examples of the super absorbent polymer include poly-N-vinylacetamide and cross-linked sodium polyacrylate. Other materials, such as cotton, polypropylene, and polyester, may also be used for the absorbent pad 12. The materials from which the absorbent pad 12 can be made may also generally include non-woven fabrics. The absorbent pad 12 may even be made from a sponge.

Figure 5:
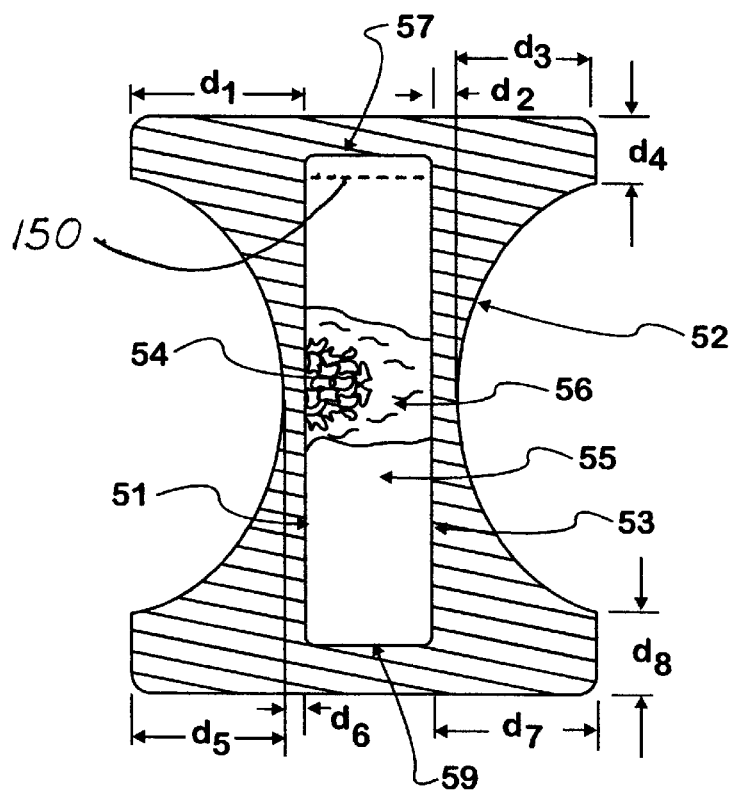
FIG. 5 is a plan view of an alternative embodiment of an absorbent thermal bag of the present invention

Referring now to FIG. 5, a schematic of an alternative embodiment of the absorbent thermal bag 10 is presented. The junction of the absorbent pad 52 and the ice bag 55 defines attachment sections 57, 59, 53 and 51. The absorbent pad 52 extends beyond the ice bag 55 thus providing an unobstructed perimeter area. The unobstructed perimeter area defines perimeter distances $d_1$, $d_3$ and $d_4$ at attachment section 57, a perimeter distance $d_2$ at attachment section 53, a perimeter distance d6 at attachment section 51, and perimeter distances $d_5$, $d_7$ and $d_8$ at attachment section 59. The unobstructed perimeter area provides an area of the absorbent pad 52 that is unobstructed by the ice bag 55. The unobstructed perimeter area allows for simultaneous, side-by-side placement of the ice bag 55 and the absorbent pad 52 on a wound site. Perimeter distances $d_1$ through $d_8$ may range from about 0.125 inches to about 5 inches (about 0.3175 cm to about 12.7000 cm), or more. The magnitude of the perimeter distances $d_1$ through $d_8$ may be different for different applications. The ice bag 55 may be attached to the absorbent pad 52 by various means as described above. In the preferred embodiment, the ice bag 55 is releasably attached to the absorbent pad 52.

The shape of the absorbent pad 52 may be described as an hour glass and is configured to accommodate the perineum. Thus it can be seen that the areas unobstructed by the ice bag 52, and described by the perimeter distances $d_1$ through $d_8$, provide an improvement over the prior art for both the absorption of bodily fluids from the perineum and providing cold therapy to the perineum. Where the ice bag 55 is attached tom the absorbent pad 52 there is a reduced absorbency, as described above.

Figure 6:
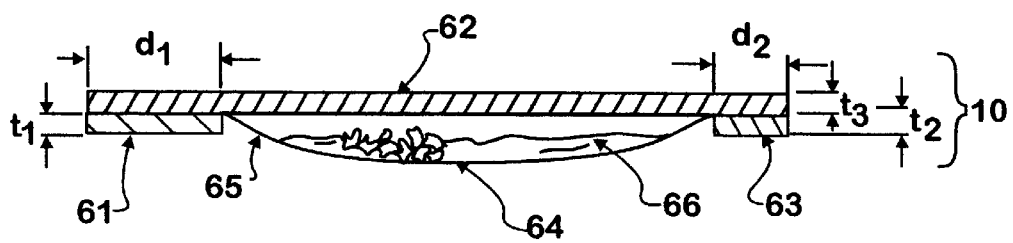
FIG. 6 is a cross-sectional schematic of an alternative embodiment of an absorbent thermal bag of the present invention.

FIG. 6 presents yet another embodiment of an absorbent ice bag 10 according to the present invention. The absorbent ice bag 10 includes an absorbent pad 62 operatively associated with an ice bag 65. The absorbent pad 62 defines a thickness $t_3$. The thickness $t_3$ may range from about 0.0625 inch to about 1 inch (about 0.3175 cm to about 1.9050 cm).

The absorbent thermal bag can further include containment pads 61, 63. The containment pads 61, 63 are attached to a side of the absorbent pad 62 that is operatively associated with the thermal bag (e.g., ice bag 65). The containment pads 61, 63 are positioned so as to focus the thermal therapy to a region of the body in need of therapy. Thus, the containment pads also provide a thermal barrier that reduces absorption of heat through the ends of the ice bag 65 from the ambient air in the case of cold therapy, or alternatively, the loss of heat through the ends of the thermal bag to the ambient air in the case of heat therapy. The containment pad 61 further defines a thickness $t_1$ and the containment pad 63 further defines a thickness $t_2$. The thickness $t_1$, $t_2$ may range from about 0.0625 inch to about 1 inch (about 0.3175 cm to about 2.5400 cm), and more, and preferably from about 0.250 inches to about 0.750 inch (about 0.6350 cm to about 1.9050 cm). The thickness $t_1$ may be equal to or different from the thickness $t_2$. The containment pads 61, 63 may be made from a material that provides a thermal barrier such as cellulosic material, felt, wool, or other suitable material.

The thermal bag (shown as an ice bag 65) may contain ice 64, or other suitable phase change material. The thermal bag 65 may also contain water 66, or other liquid that results from melting of the phase change material for example.

Figure 7:
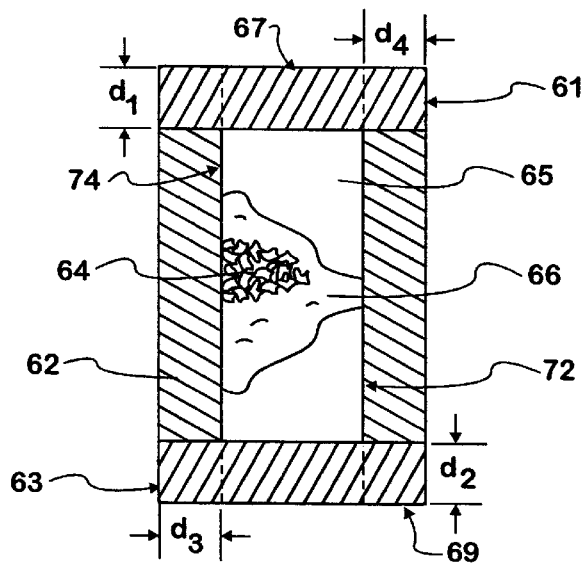
FIG. 7 is a plan view of the absorbent thermal bag of FIG. 6.

Referring now to FIG. 7, the ice bag 65 of FIG. 6 is depicted in plan view. As illustrated, the junction of the absorbent pad 62 and the thermal bag 65 defines attachment sections 67, 69, 72 and 74. The absorbent pad 62 extends beyond the thermal bag 65 thus providing an unobstructed perimeter area. The unobstructed perimeter area defines a perimeter distance d1 at attachment section 67, a perimeter distance d2 at attachment section 69, a perimeter distance d3 at attachment section 74, and a perimeter distance d4 at attachment section 72. The unobstructed perimeter area provides an area of the absorbent pad 62 that is unobstructed by the thermal bag 65. Such an unobstructed are allows for simultaneous, side-by-side, placement of the thermal bag 65 and the absorbent pad 62 on a wound site. Perimeter distances d1, d2, d3 and d4 may range from about 0.125 inch to about 5 inches (about 0.3175 cm to about 12.7000 cm), or more. The magnitude of the perimeter distances d1, d2, d3 and d4 may be different for different applications.

Figure 6A:
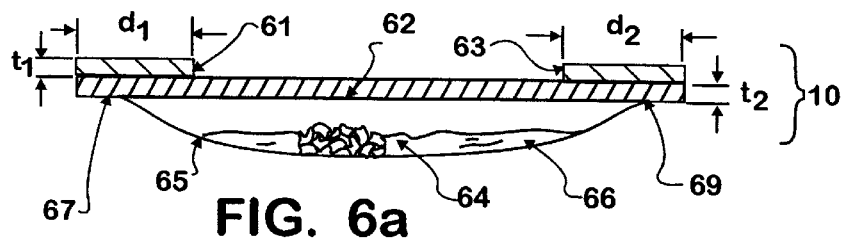
FIG. 6a is a cross-sectional view of an alternative embodiment of the absorbent thermal bag of FIG. 6.

Referring now to FIG. 6a, an alternative embodiment of the absorbent thermal bag 10 of FIG. 6 is illustrated. The components of the embodiment illustrated in FIG. 6a are the same as those identified in FIG. 6. The thickness and perimeter distances defined by the embodiment illustrated in FIG. 6a are also the same as those identified in FIG. 6. Thus, the absorbent ice bag 10 includes an absorbent pad 62 operatively associated with an ice bag 65 and containment pads 61, 63. As described above, the containment pads 61, 63 are positioned so as to focus the cold therapy to a region of the body in need of therapy. In the embodiment illustrated in FIG. 6a, the containment pads 61, 63 are attached to a side of the absorbent pad 62 that is opposite the side of the absorbent pad operatively associated with the ice bag 65.

As described above, the ice bag 65 may contain ice 64, or other suitable phase change material. The ice bag 65 may also contain water 66, or other liquid that results from melting of the phase change material.

Figure 8:
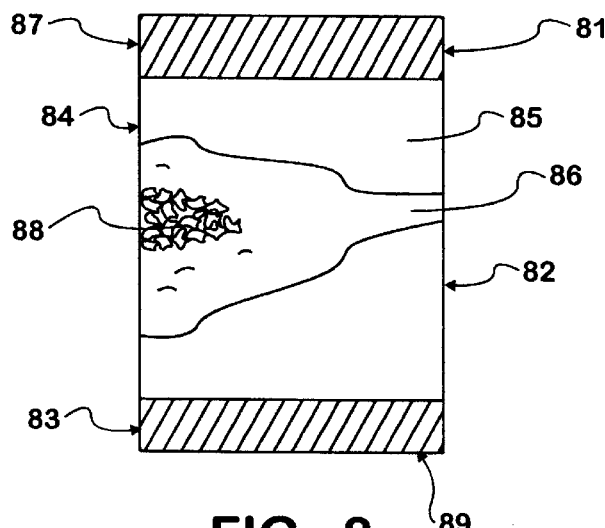
FIG. 8 is an alternative embodiment of the absorbent thermal bag of FIG. 7.
Figure 8A:
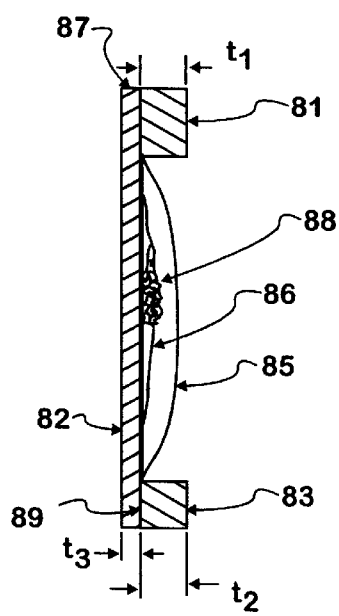
FIG. 8a is a cross-sectional side view of the absorbent thermal bag of FIG. 8.

FIGS. 8 and 8a illustrate yet another embodiment of the absorbent ice bag 10 of the present invention. The absorbent ice bag 10 includes an absorbent pad 82 operatively associated with an ice bag 85. The absorbent pad 82 defines a thickness $t_3$. The thickness $t_3$ may range from about 0.125 inch to about 1 inch (about 0.3175 cm to about 2.5400 cm), and more, and preferably from about 0.250 inch to about 0.750 inch (about 0.6350 cm to about 1.9050 cm).

The absorbent ice bag 10 further includes containment pads 81, 83. The containment pads 81, 83 are attached to a side of the absorbent pad 82 that is operatively associated with the ice bag 85. The containment pads 81, 83 are positioned so as to focus the cold therapy to a region of the body in need of therapy. Thus, the containment pads also provide a thermal barrier that reduces absorption of heat through the ends of the ice bag 85 from the ambient air. The containment pad 81 further defines a thickness $t_1$ and the containment pad 83 further defines a thickness $t_2$. The thickness $t_1$, $t_2$ may range from about 0.125 inch to about 1 inch (about 0.3175 cm to about 2.5400 cm), and more, and preferably from about 0.250 inch to about 0.750 inch (about 0.6350 cm to about 1.9050 cm). The thickness $t_1$ may be equal to or different from the thickness $t_2$.

As provided with the other embodiments of the present invention, the ice bag 85 may contain ice 84, or other suitable phase change material. The ice bag 85 may also contain water 86, or other liquid that results from melting of the phase change material.

Figure 9:
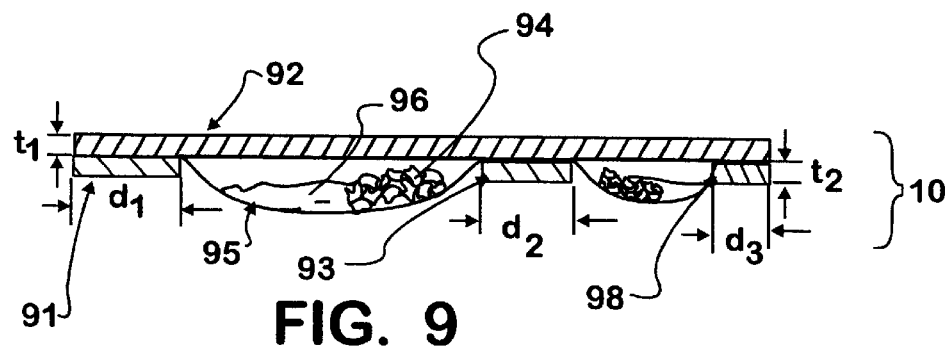
FIG. 9 is a cross-sectional schematic of an alternative embodiment of an absorbent thermal bag of the present invention.
Figure 9A:
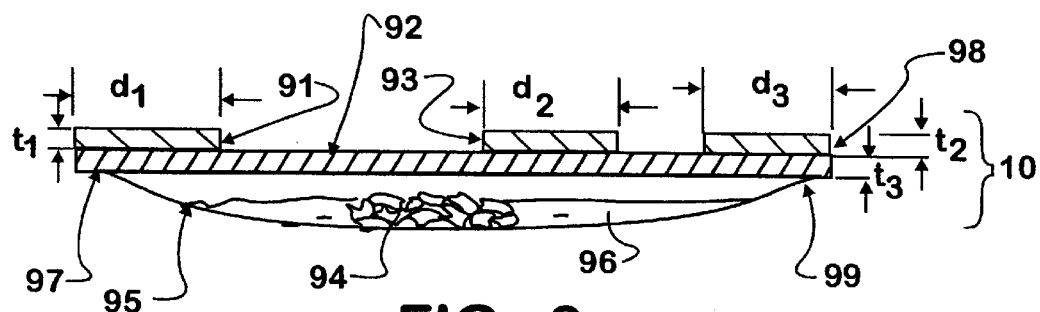
FIG. 9a is a cross-sectional view of an alternative embodiment of an absorbent thermal bag of the present invention.
Figure 10:
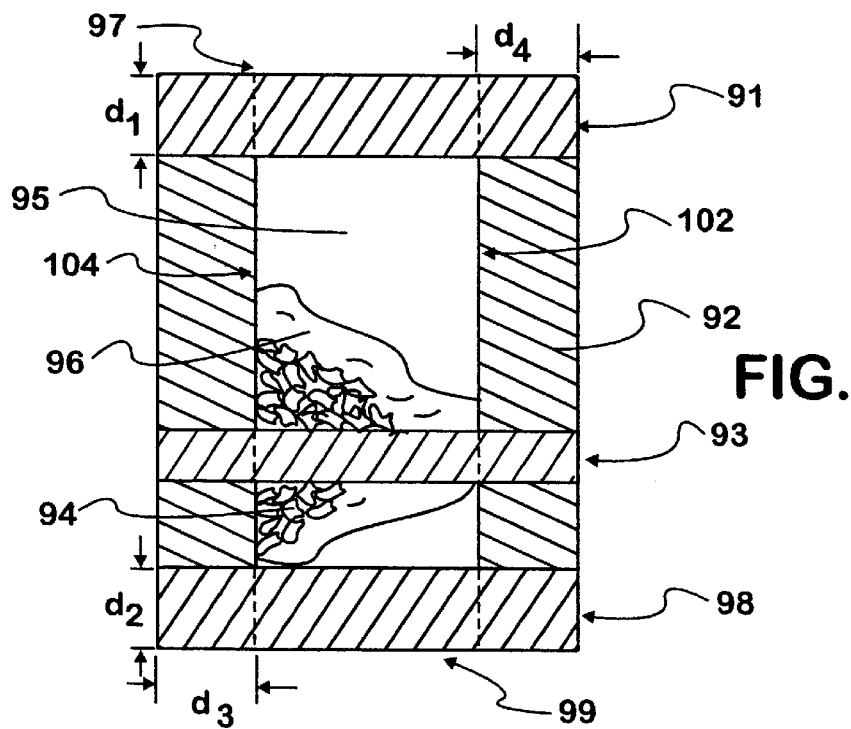
FIG. 10 is a plan view of the absorbent thermal bag of FIG. 9.

FIGS. 9, 9a and 10 illustrate embodiments of the absorbent ice bag 10 that include more than two containment pads. The absorbent ice bag 10 includes an absorbent pad 92 operatively associated with an ice bag 95. The absorbent pad 92 defines a thickness $t_3$. The thickness $t_3$ may range from about 0.1265 inch to about 1 inch (about 0.3175 cm to about 2.5400 cm), and more, and preferably from about 0.250 inch to about 0.750 inch (about 0.6350 cm to about 1.9050 cm).

The absorbent ice bag 10 further includes containment pads 91, 93, 98. The containment pads 91, 93, 98 may be attached to a side of the absorbent pad 92 that is operatively associated with the ice bag 95, as shown in FIG. 9. In an alternative embodiment, the containment pads 91, 93, 98 may be attached to a side of the absorbent pad 92 that is opposite the side of the absorbent pad 92 that is operatively associated with the ice bag 95, as shown in FIG. 9a. As described above, the containment pads 91, 93, 98 are positioned so as to focus the cold therapy to a region of the body in need of therapy. The containment pad 91 further defines a thickness $t_1$, the containment pad 93 further defines a thickness $t_4$ (not illustrated), and the containment pad 98 further defines a thickness $t_2$. The thickness $t_1$, $t_2$ and $t_4$ may range from about 0.0625 inch to about 1 inch (about 0.3175 cm to about 2.5400 cm), and more, and preferably from about 0.250 inch to about 0.750 inch (about 0.6350 cm to about 1.9050 inch). The thickness $t_1$, $t_2$, $t_4$ may be equal or different.

The ice bag 95 may contain ice 94, or other suitable phase change material. The ice bag 95 may also contain water 96 or other liquid that results from melting of the phase change material.

Referring now to FIG. 10, the ice bag 65 of FIG. 9 is depicted in plan view. As illustrated, the junction of the absorbent pad 92 and the ice bag 95 define attachment sections 97, 99, 102 and 104. The absorbent pad 92 extends beyond the ice bag 95 thus providing an unobstructed perimeter area. The unobstructed perimeter area defines a perimeter distance $d_1$ at attachment section 97, a perimeter distance $d_2$ at attachment section 99, a perimeter distance $d_3$ at attachment section 104, and $d_4$ at attachment section 102. The unobstructed perimeter area provides an area of the absorbent pad 92 that is unobstructed by the ice bag 95. Such an unobstructed are allows for simultaneous, side-by-side placement of the ice bag 95 and the absorbent pad 92 on a wound site. Perimeter distances $d_1$, $d_2$, $d_3$ and $d_4$ may range from about 0.125 inch to about 5 inches (about 0.3175 cm to about 12.7000 cm), or more. The magnitude of the perimeter distances $d_1$, $d_2$, $d_3$, and $d_4$ may be different for different applications.

Figure 11:
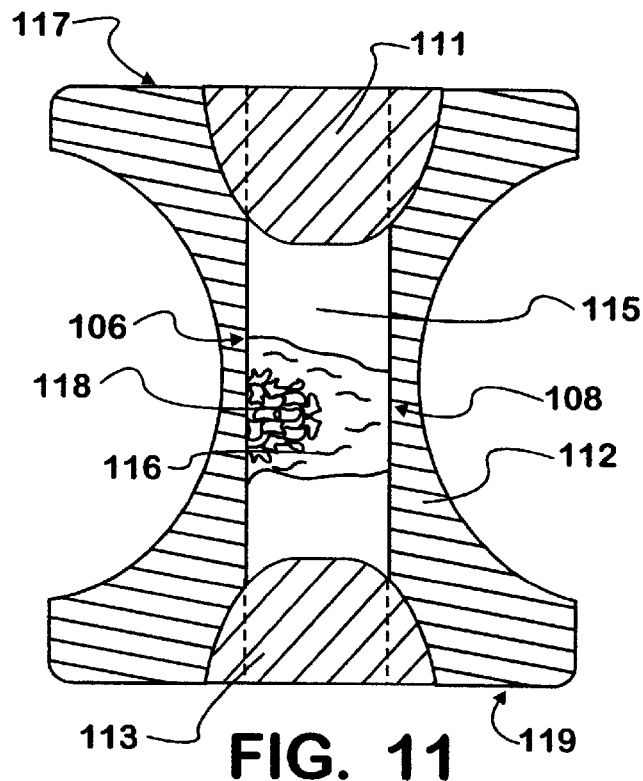
FIG. 11 is an alternative embodiment of the absorbent thermal bag of FIG. 10.
Figure 12:
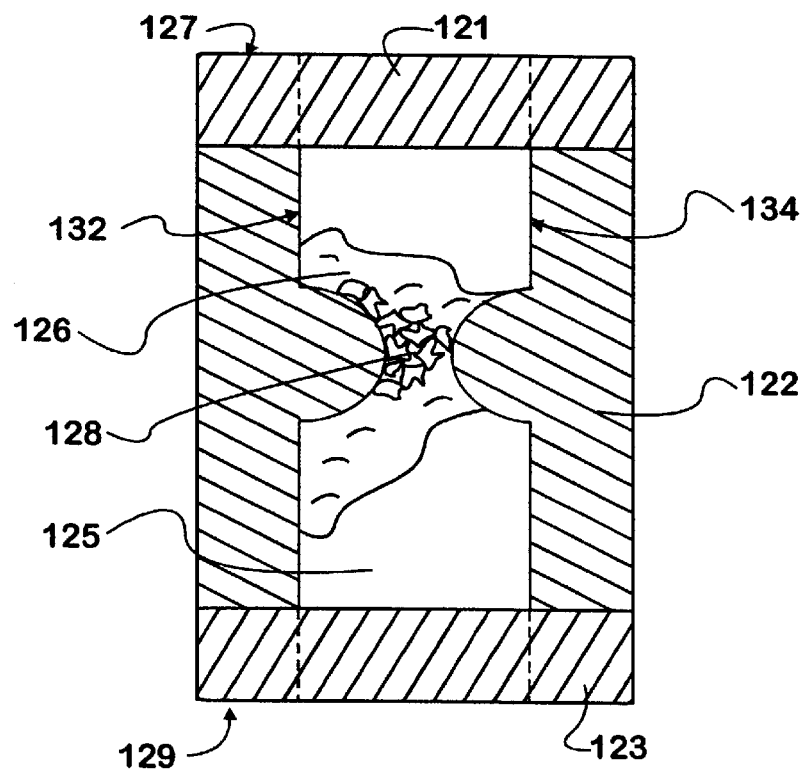
FIG. 12 is an alternative embodiment of the absorbent thermal bag of FIG. 10.
Figure 13:
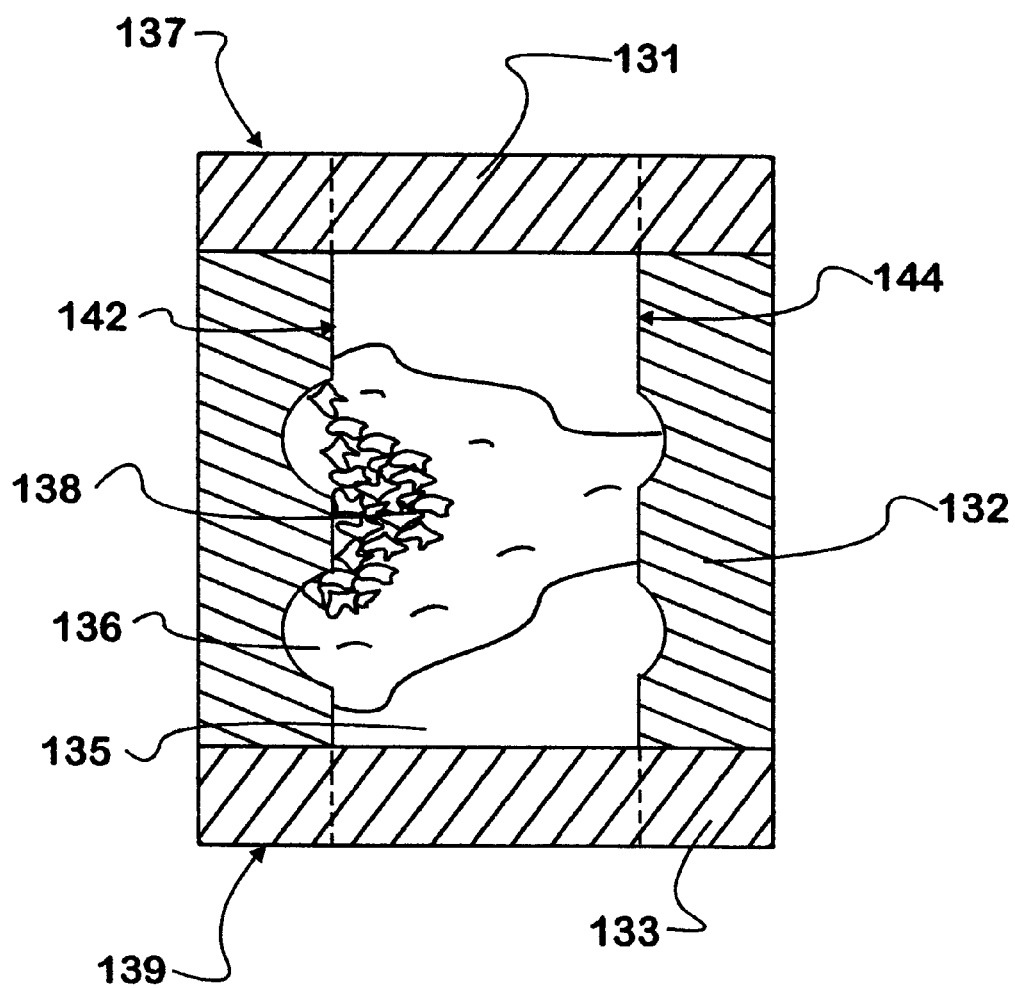
FIG. 13 is an alternative embodiment of the absorbent thermal bag of FIG. 10.

Referring to FIGS. 11, 12 and 13, alternative embodiments of the absorbent ice bag 10 that include containment pads are shown. In FIG. 11, the junction of the absorbent pad 112 and the ice bag 115 defines attachment sections 117, 119, 106 and 108. The absorbent pad 112 extends beyond the ice bag 115 at attachment sections 117, 119, 106 and 108 thus forming areas unobstructed by the ice bag 1156. As described above, such unobstructed areas allow for simultaneous, side-by-side placement of the ice bag 115 and the absorbent pad 112 on a wound site. In one embodiment, the ice bag 115 is releasably attached to the absorbent pad 112.

The shape of the absorbent pad 112 may be described as an hour glass and is configured to accommodate the perineum. Thus it can be seen that that areas unobstructed by the ice bag 112 provide an improvement over the prior art for both absorption of bodily fluids from the perineum and providing cold therapy to the perineum. Where the ice bag 115 is attached to the absorbent pad 1123 there is a reduced absorbency, as described above.

The absorbent ice bag 10 further includes containment pads 111, 113. The containment pads 111, 113 maybe attached to a side of the absorbent pad 112 that is operatively associated with the ice bag 115, as shown in FIG. 11. In an alternative embodiment (not shown), the containment pads 111, 113 may be attached to a side of the absorbent pad 112 that ism opposite the side of the absorbent pad 112 that is operatively associated with the ice bag 115. As described above, the containment pads 111, 113 are positioned so as to focus cold therapy to a region of the body in need of therapy. The containment pads may be adapted to a semi-circular shape, as shown, to better accommodate, for example, the perineum. However, the containment pads 111, 113 may be adapted to other shapes to accommodate other areas of a person's body.

Likewise, FIG. 12 illustrates an embodiment of the absorbent ice bag 10 that is shaped to accommodate an area of the human body. The junction of the absorbent pad 122 and the ice bag 125 defines attachment sections 127, 129, 126 and 128. The absorbent pad 122 extends beyond the ice bag 125 at attachment section 127, 129, 126 and 128 thus forming areas unobstructed by the ice bag 125. As described above, such unobstructed areas allow for simultaneous, side-by-side placement of the ice bag 125 and the absorbent pad 122 on a wound site. In one embodiment, the ice bag is releasably attached to the absorbent pad 122.

The shape of the ice bag 125 may be described as an hour glass and is configured to accommodate, for example, the perineum Thus it can be seen that the ice bag 125 and the areas unobstructed by the ice bag 125 provide an improvement, for example, over the prior art for both the absorption an of bodily fluids from the perineum and providing cold therapy to the perineum.

The absorbent ice bag 10 further includes containment pads 121, 123. The containment pads 121, 123 may be attached to a side of the absorbent pad 122 that is operatively associated with the ice bag 125, as shown in FIG. 12. In an alternative embodiment (not shown), the containment pads 121, 123 may be attached to a side of the absorbent pad 122 that is opposite the side of the absorbent pad 122 that is operatively associated with the ice bag 125. As described above, the containment pads 121, 123 are positioned so as to focus the cold therapy to a region of the body in need of therapy.

Similarly, FIG. 13 illustrates yet another embodiment of the absorbent ice bag 10 that is shaped to accommodate an area of the human body. The junction of the absorbent pad 132 and the ice bag 135 defines attachment sections 137, 139, 142 and 144. The absorbent pad 132 extends beyond the ice bag 135 at attachment section 137, 139, 142 and 144 thus forming areas unobstructed by the ice bag 135. As described above, such unobstructed areas allow for simultaneous, side-by-side placement of the ice bag 135 and the absorbent pad 132 on a wound site. In the preferred embodiment, the ice bag 135 is releasably attached to the absorbent pad 132.

The shape of the iced bag 135 may be described as a double hour glass and is configured to accommodate, for example, the perineum and the rectum. Thus, it can be seen that the ice bag 135 and the areas unobstructed by the ice bag 135 provide an improvement, for example, over the prior art for both the absorption of bodily fluids from the perineum and the rectum and providing cold therapy to the perineum and the rectum.

The absorbent ice bag 10 further includes containment pads 131, 133. The containment pads 131, 133 may be attached to a side of the absorbent pad 132 that is operatively associated with the ice bag 135, as shown in FIG. 12. In an alternative embodiment (not shown), the containment pads 131, 133 may be attached to a side of the absorbent pad 132 that is opposite the side of the absorbent pad 132 that is operatively associated with the ice bag 135. As described above, the containment pads 131, 133 are positioned so as to focus the cold therapy to a region of the body in need of therapy.

As with each of the embodiments described above, ice bags 115, 125, 135 may contain ice 118, 128, 138 or other suitable phase change material. Ice bags 115, 125, 135 may also contain water 116, 126, 136, or other liquid that results from melting of the phase change material.

The absorbent thermal bag of the present invention may be attached to the body of the person requiring thermal therapy. Any of the means for attachment known in the art may be suitable for use with the absorbent thermal bag of the present invention. Accordingly, ties or straps may be used as attachment means. Hook and loop fasteners may be used to attach the absorbent thermal bag to a person's garment. Alternatively, the absorbent thermal bag may be held in place by a person's garment, such as an under garment. other attachment means developed in the art may also provide suitable means to attach the absorbent thermal bag to the body of a person requiring thermal therapy.

The Figures illustrate the invention using a thermal bag which contains ice (i.e., "ice bag") as a phase change material for cold therapy. It will be understood that the invention likewise applies the use of exothermic materials in the thermal bag for heat therapy alternatively, and the presence of ice/water in the illustrations is not to be construed as a limitation of the absorbent thermal bag to the use of ice or other phase change materials.

Industrial Applicability

There has been provided, in accordance with the present invention, a low cost absorbent thermal bag that provides for both cold or hot therapy and the absorption of bodily fluids from wound sites. The present invention provides a thermal pack that can be regenerated in situ. The present invention provides a thermal pack that allows the simultaneous placement of the pack and an absorbent pad on the injury site. The present invention further provides a low cost thermal pack that can be regenerated in situ and allows the simultaneous placement of the cold pack and the absorbent pad on the injury site.

While the invention has been described with specific embodiments, many alternatives, modifications and variations will be apparent to those skilled in the art in light of the foregoing description. Accordingly, it is intended to include all such alternatives, modifications and variations set forth within the spirit and scope of the appended claims.

What is claimed is:

1. An absorbent thermal bag comprising:
   a thermal bag defining a single-side surface area, the thermal bag further defining a resealable opening;
   an absorbent pad attached to the thermal bag, the absorbent pad defining a pad area such that the pad area is larger than the single side surface area, the pad area defining an area difference that is the difference between the pad area and the single side surface area; and
   an unobstructed perimeter area formed from the area difference;
   wherein an exothermic material is to be added to the thermal bag through the resealable opening and wherein the unobstructed perimeter area provides an unobstructed area for absorbing a bodily fluid on the absorbent pad.

2. The absorbent thermal bag of claim 1 wherein the unobstructed perimeter area defines at least four perimeter distances $d_1$, $d_2$, $d_3$ and $d_4$, the perimeter distances $d_1$, $d_2$, $d_3$ and $d_4$ being from about 0.125 inch to about 5 inches.

3. The absorbent thermal bag of claim 1 wherein the perimeter distances $d_1$, $d_2$, $d_3$ and $d_4$ are at least 0.125 inch.

4. The absorbent thermal bag of claim 1 wherein the absorbent pad defines a thickness t, the thickness t being from about 0.0625 inch to about 1 inch.

5. The absorbent thermal bag of claim 4 wherein the thickness t is from about 0.250 inch to about 0.750 inch.

6. The absorbent thermal bag of claim 1 wherein the absorbent pad comprises a super absorbent polymer.

7. The absorbent thermal bag of claim 1 wherein the absorbent pad comprises a material selected from the group consisting of cellulose, cellulose derivatives, cotton, polypropylene, polyester, poly-N-vinylacetamide, cross-linked sodium polyacrylate, and combinations thereof.

8. The absorbent thermal bag of claim 1 wherein the ice bag comprises a material selected from the group consisting of polyethylene, polyester, polypropylene, cellulose esters, cellulose ethers, nylon, polyvinyl alcohol acetals, polyvinyl chloride, polyvinyl chloride acetate, polystyral, methyl methacrylate, polyvinylidene chloride, ethylene octene copolymers, and combinations thereof.

9. The absorbent thermal bag of claim 8 wherein the material is metallized.

10. The absorbent thermal bag of claim 1 wherein the exothermic material is a phase change material, exothermic dissolving solute in solvent composition, or latent heat storage material.

11. The absorbent thermal bag of claim 10 wherein the exothermic materials is an exothermic phase change material selected from the group consisting of sodium thiosulfate pentahydrate and sodium acetate trihydrate.

12. The absorbent thermal bag of claim 10 wherein the exothermic material is an exothermic dissolving solute in solvent selected from the group consisting of calcium chloride and water, ammonium sulfate and water, and magnesium sulfate and water.

13. The absorbent thermal bag of claim 10 wherein the exothermic material is a latent heat storage material selected from the group consisting of pre-warmed water and pre-warmed oil.

14. The absorbent thermal bag of claim 1 wherein the absorbent pad is hour glass shaped.

15. The absorbent thermal bag of claim 1 wherein the ice bag is hour glass shaped.

16. The absorbent thermal bag of claim 1 wherein the ice bag is double hour glass shaped.

17. An absorbent thermal bag comprising:
a thermal bag defining a single-side surface area, the thermal bag further defining a resealable opening;
an absorbent pad attached to the thermal bag, the absorbent pad defining a pad area such that the pad area is larger than the single-side surface area, the pad area further defining a pad area such that the pad area is larger than the single side surface area, the pad area further defining an area difference that is the difference in area between the pad area and the single side surface area;
an unobstructed perimeter are formed from the area difference;
a first releasable fastener attached to the thermal bag; and
a second releasable fastener attached to the absorbent pad;
wherein an exothermic material is to be added to the ice bag through the resealable opening, wherein the unobstructed perimeter area provides an unobstructed area for absorbing a bodily fluid on the absorbent pad, and further wherein the first releasable fastener and the second releasable fastener releasably attach the absorbent pad to the thermal bag.

18. The absorbent thermal bag of claim 17 wherein the first releasable fastener and second releasable fastener are hook and loop fasteners.

19. The absorbent thermal bag of claim 17 wherein the unobstructed perimeter area defines at least four perimeter distances d1, d2, d3 and d4, the perimeter distances $d_1$, $d_2$, $d_3$ and $d_4$ being from about 0.125 inch to about 5 inches.

20. The absorbent thermal bag of claim 17 wherein the perimeter distances $d_1$, $d_2$, $d_3$ and $d_4$ are at least 0.125 inch.

21. The absorbent thermal bag of claim 17 wherein the absorbent pad defines a thickness t, the thickness t being from about 0.0625 inch to about 1 inch.

22. The absorbent thermal bag of claim 21 wherein the thickness t is from about 0.250 inch to about 0.750 inch.

23. The absorbent thermal bag of claim 17 wherein the absorbent pad comprises a super absorbent polymer.

24. The absorbent thermal bag of claim 17 wherein the absorbent pad comprises a material selected from the group consisting of cellulose, cellulose derivatives, cotton, polypropylene, polyester, poly-N-vinylacetamide, cross-linked sodium polyacrylate, and combinations thereof.

25. The absorbent thermal bag of claim 17 wherein the ice bag is manufactured from a material selected from the group consisting of polyethylene, polyester, polypropylene, cellulose esters, cellulose ethers, nylon, polyvinyl alcohol acetals, polyvinyl chloride, polyvinyl chloride acetate, polystyral, methyl methacrylate, polyvinylidene chloride, ethylene octene copolymers, and combinations thereof.

26. The absorbent thermal bag of claim 25 wherein the material is metallized.

27. The absorbent thermal bag of claim 17 wherein the exothermic material is an exothermic phase change material, exothermic dissolving solute in solvent composition, and latent heat storage material.

28. The absorbent thermal bag of claim 27 wherein the exothermic material is an exothermic phase change material selected from the group consisting of sodium thiosulfate pentahydrate and sodium acetate trihydrate.

29. The absorbent thermal bag of claim 27 wherein the exothermic material is an exothermic dissolving solute in solvent selected from the group consisting of calcium chloride and water, ammonium sulfate and water, and magnesium sulfate and water.

30. The absorbent thermal bag of claim 27 wherein the exothermic material is a latent heat storage material selected from the group consisting of pre-warmed water and pre-warmed oil.

31. The absorbent thermal bag of claim 17 wherein the absorbent pad is hour glass shaped.

32. The absorbent thermal bag of claim 17 wherein the ice bag is hour glass shaped.

33. The absorbent thermal bag of claim 17 wherein the ice bag is double hour glass shaped.

34. An absorbent thermal bag for heat therapy, the absorbent thermal bag comprising:
a thermal bag defining a single-side surface area, the thermal bag further defining a resealable opening;
an absorbent pad attached to the thermal bag, the absorbent pad defining a pad area such that the pad area is larger than the single side surface area, the pad area further defining an area difference that is the difference in area between the pad area and the single-side surface area;
an unobstructed perimeter area formed from the area difference; and
at least a first containment pad and a second containment pad attached to the absorbent thermal bag;
wherein an exothermic material is to be added to the ice bag through the resealable opening, wherein the unobstructed perimeter area provides an unobstructed area for absorbing a bodily fluid on the absorbent pad, and wherein the containment pads focus the heat therapy.

35. The absorbent thermal bag of claim 34 wherein the unobstructed perimeter area defines at least four perimeter distances $d_1$, $d_2$, $d_3$ and $d_4$ the perimeter distances $d_1$, $d_2$, $d_3$ and $d_4$ being from about 0.125 inch to about 5 inches.

36. The absorbent thermal bag of claim 34 wherein the perimeter distances $d_1$, $d_2$, $d_3$ and $d_4$ are at least 0.125 inch.

37. The absorbent thermal bag of claim 34 wherein the absorbent pad defines a thickness t, the thickness t being from about 0.0625 to about 1 inch.

38. The absorbent thermal bag of claim 37 wherein the thickness t is from about 0.250 inch to about 0.750 inch.

39. The absorbent thermal bag of claim 34 wherein the absorbent pad comprises a super absorbent polymer.

40. The absorbent thermal bag of claim 34 wherein the absorbent pad comprises a material selected from the group consisting of cellulose, cellulose derivatives, cotton, polypropylene, polyester, poly-N-vinylacetamide, cross-linked sodium polyacrylate and combinations thereof.

41. The absorbent thermal bag of claim 34 wherein the ice bag is manufactured from a material selected from the group consisting of polyethylene, polyester, polypropylene, cellulose esters, cellulose ethers, nylon, polyvinyl alcohol acetals, polyvinyl chloride, polyvinyl chloride acetate, polystyral, methyl methacrylate, polyvinylidene chloride, ethylene octene copolymers, and combinations thereof.

42. The absorbent thermal bag of claim 41 wherein the material is metallized.

43. The absorbent thermal bag of claim 34 wherein the exothermic material is an exothermic phase change material exothermic dissolving solute in solvent composition, or latent heat storage material.

44. The absorbent thermal bag of claim 43 wherein the exothermic material is an exothermic phase change material selected from the group consisting of sodium thiosulfate pentahydrate and sodium acetate trihydrate.

45. The absorbent thermal bag of claim 43 wherein the exothermic material is an exothermic dissolving solute in solvent selected from the group consisting of calcium chloride and water, ammonium sulfate and water, and magnesium sulfate and water.

46. The absorbent thermal bag of claim 43 wherein the exothermic material is a latent heat storage material selected from the group consisting of pre-warmed water and pre-warmed oil.

47. The absorbent thermal bag of claim 34 wherein the absorbent pad is hour glass shaped.

48. The absorbent thermal bag of claim 34 wherein the ice bag is hour glass shaped.

49. The absorbent thermal bag of claim 34 wherein the ice bag is double hour glass shaped.

50. The absorbent thermal bag of claim 34 wherein the first containment pad defines a thickness $t_1$, the thickness $t_1$ being from about 0.0625 inch to about 0.750 inch.

51. The absorbent thermal bag of claim 50 wherein the thickness $t_1$ is from about 0.250 inch to about 0.500 inch.

52. The absorbent thermal bag of claim 34 wherein the second containment pad defines a thickness $t_2$, the thickness $t_2$ being from about 0.0625 inch to about 0.750 inch.

53. The absorbent thermal bag of claim 52 wherein the thickness $t_2$ is from about 0.250 inch to about 0.500 inch.

* * * * *